United States Patent [19]
Jefferies, Sr.

[11] 3,936,737
[45] Feb. 3, 1976

[54] CORROSION MONITORING SYSTEM
[75] Inventor: Fitch B. Jefferies, Sr., Springfield, N.J.
[73] Assignee: C.M.S. Inc., Springfield, N.J.
[22] Filed: Apr. 10, 1975
[21] Appl. No.: 566,832

[52] U.S. Cl. ............................................. 324/65 CR
[51] Int. Cl.² ........................................ G01R 27/02
[58] Field of Search .......... 324/65 CR, 71 R; 73/86; 204/195 C; 23/253 C, 230 C

[56] References Cited
UNITED STATES PATENTS

| | | | |
|---|---|---|---|
| 2,878,354 | 3/1959 | Ellison | 324/65 CR |
| 2,982,930 | 5/1961 | Wygant | 324/65 CR |
| 3,104,355 | 9/1963 | Holmes et al. | 324/65 CR |
| 3,153,217 | 10/1964 | Cramer et al. | 324/65 CR |
| 3,155,934 | 11/1964 | Messick et al. | 324/65 CR |
| 3,220,570 | 5/1967 | Lied, Jr. | 324/65 CR |
| 3,854,087 | 12/1974 | Frenck et al. | 324/65 CR |

*Primary Examiner*—Stanley T. Krawczewicz
*Attorney, Agent, or Firm*—Lane, Aitken, Dunner & Ziems

[57] ABSTRACT

A corrosion measuring system is disclosed which includes a sensor supportable in a fluid within a vessel, such as a pipe. The sensor is generally tubular, one end of which is closed. The closed end comprises a measuring portion having a wall of relatively medium or heavy thickness. The measuring portion adjoins a relatively thick-walled outer end hub portion having a substantial radial dimension and a relatively low or negligible resistance. A resistive element is attached to the sensing element within the sensor. In combination with electrical circuitry, the probe produces readings representative of the corrosion of the sensing element which readings are correlated to the corrosion of the vessel. Another aspect of the invention relates to a multi-range bridge circuit for use with the resistive components of the probe. Effectively, the electrical resistivity of the measuring portion and the hub portion of the sensor are precalculated to be a low percentage, e.g. about 1 to 10 per cent, of the total resistance of these portions and the resistive element, so that effect of temperature variations compared to corrosion is negligible. The measuring section of the sensor is sized to be structurally sound and compatible with a predesignated bridge for a given material and anticipated corrosion rate to be useful in measuring corrosion over a plurality of ranges to produce a longer lasting probe. The method of determining the sensor parameters and the bridge components is also disclosed.

15 Claims, 6 Drawing Figures

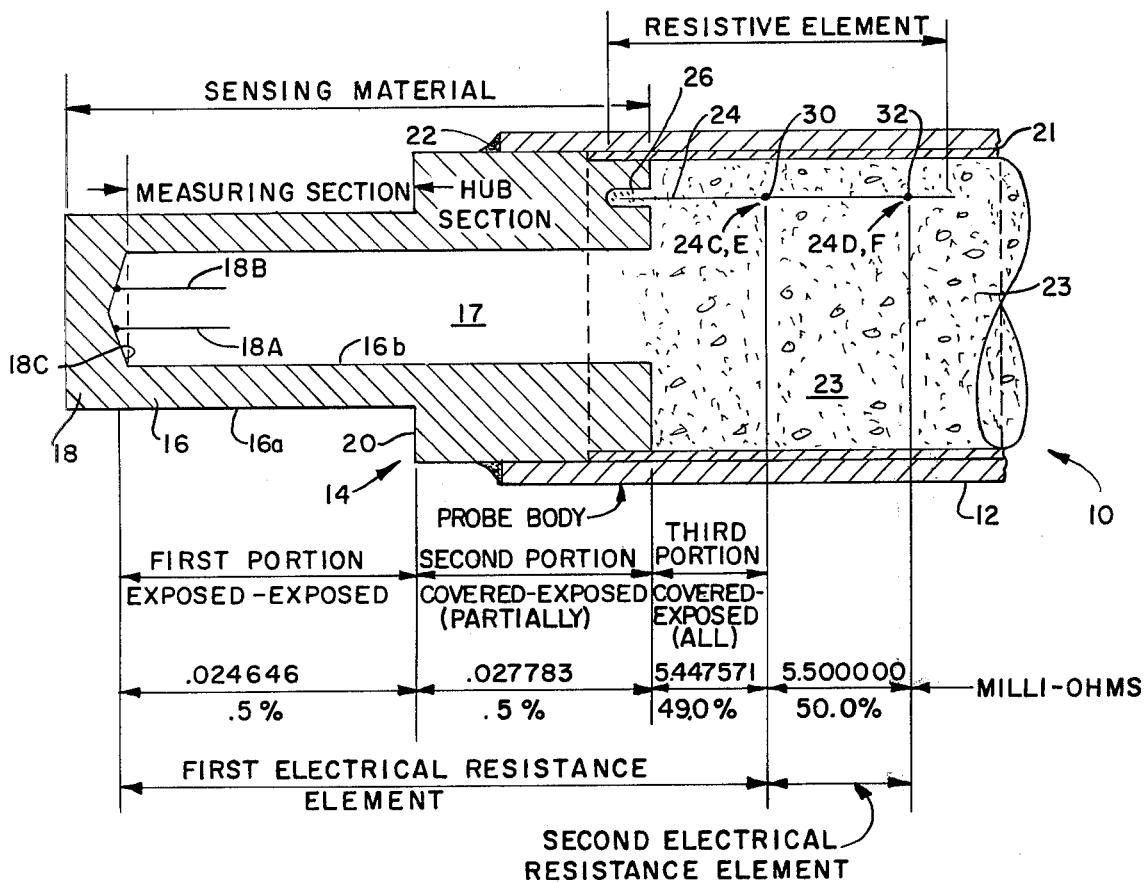
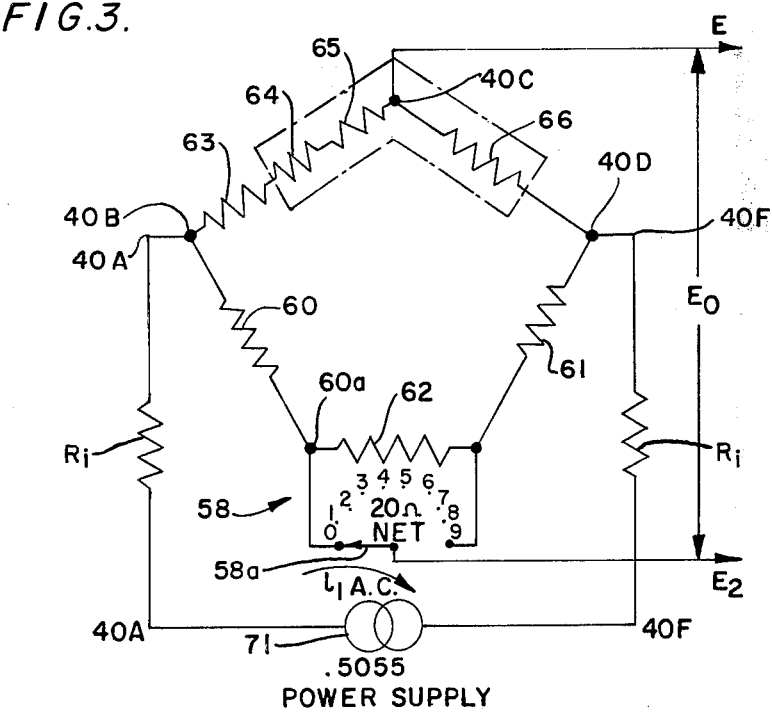

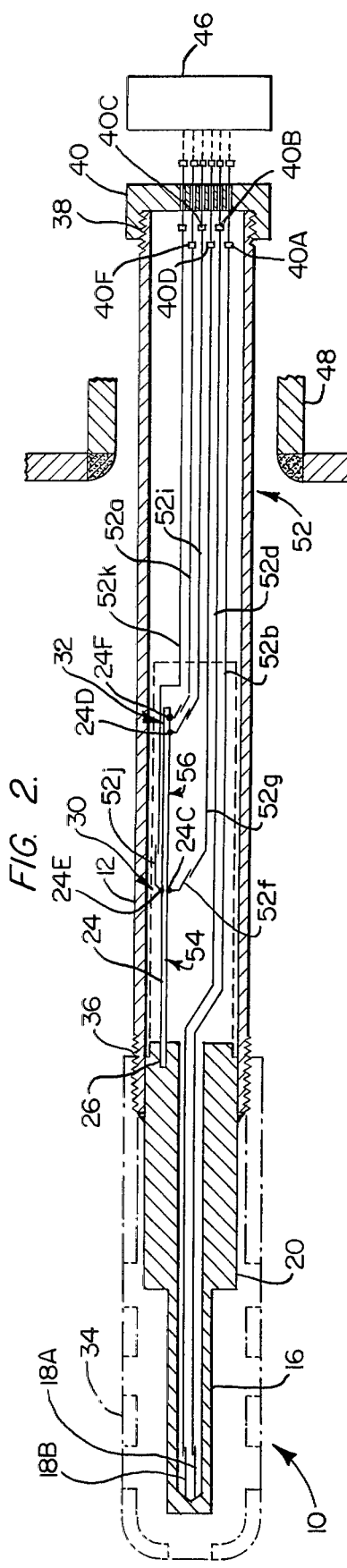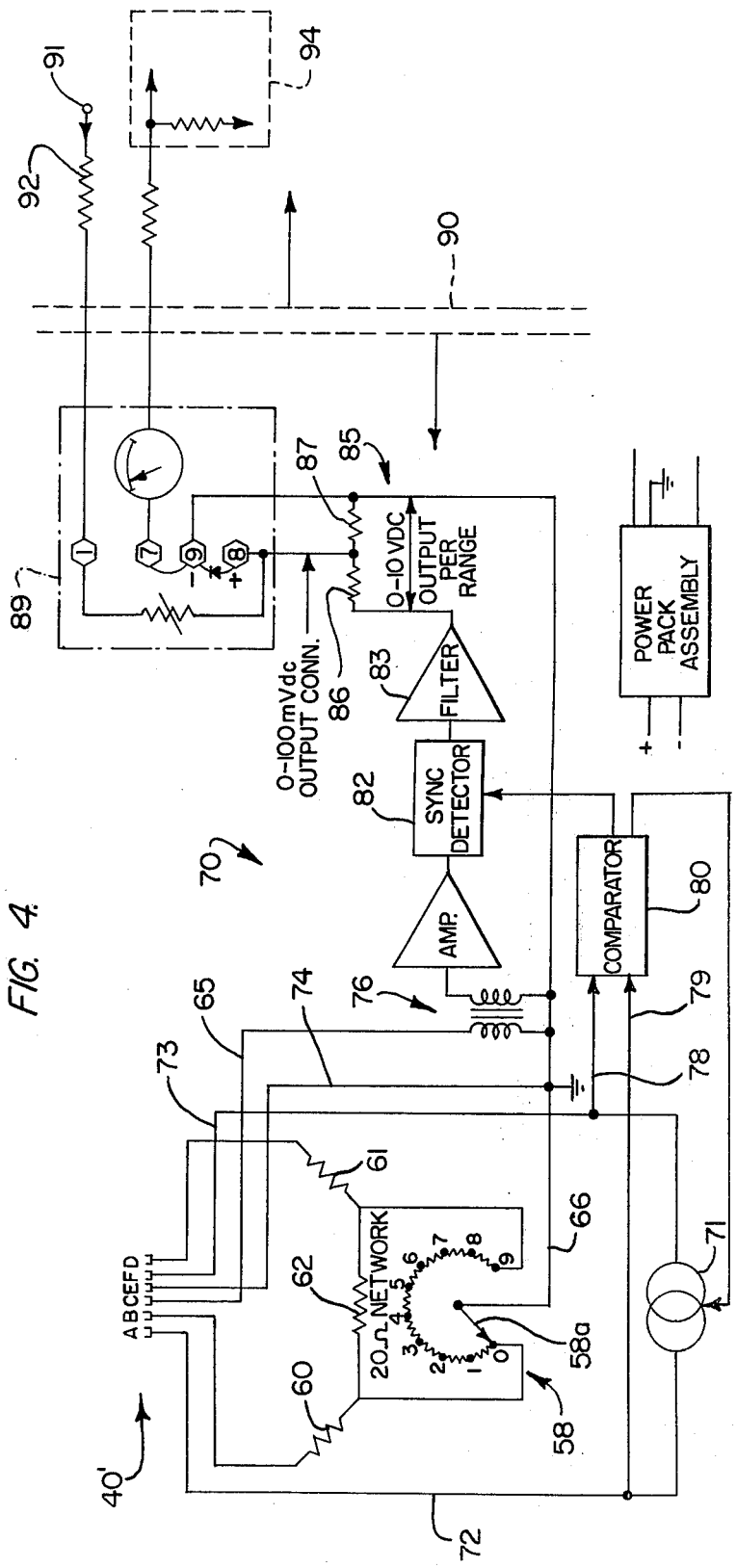

CORROSION MONITORING SYSTEM

BACKGROUND OF THE INVENTION

This invention relates to a corrosion measuring sensor. More particularly, this invention relates to a corrosion measuring probe in combination with a predesignated bridge circuit. Still more particularly, this invention relates to a corrosion measuring sensor sized to be compatible with a predesignated bridge circuit over a plurality of ranges for a given material and anticipated corrosion rate.

Early methods of determining the corrosive or other effects of fluids involved complicated efforts both in the field and laboratory. Thus, in some circumstances, fluid samples from field locations were taken to a laboratory for testing. By another method, a piece of test metal, sometimes referred to as a coupon, was immersed in the fluid for a recorded time duration at a field location, then removed from the fluid and subjected to a laboratory determination of the changes which occurred in the coupon during its immersion. From such data, the corrosivity of the fluid could be estimated.

More recently, corrosion measuring probes of various designs have been fixedly installed in the walls of processing equipment so that the somewhat fragile and delicate metal sensing elements of the probe project into the fluid. The metal of the sensing elements is preferably the same as the metal from which the process equipment is made, and preferably has the same electrical resistance characteristic, so that the corrosion of the sensing element, because of its increased resistance resulting from corrosion, is indicative of the extent of corrosion of the similar metal within the process equipment. A representative example of such a probe is described in U.S. Pat. No. 3,320,570 to E. B. Lied, Jr.

Suitable electrical instruments have been connected to such probes to measure and indicate the extent of the increase in resistance of the sensing element, using primarily null-balance and servo-balance techniques. Such electrical instruments, or at least substantial parts thereof, have heretofore been separate from the probes, but with plug facilities by means of which one set of instruments could be separately plugged to different probes to determine the resistance values of their sensing elements. The prior art contains a wide variety of bridge circuits for use in combination with probes of various designs.

While the probe and circuit combination of the present invention may be generally applied as described above, the invention has a special adaptability which includes at least some of the electrical circuitry within and as parts of the unitary probe structure, or permanently installed in the immediate vicinity thereof.

It is a feature of this invention to provide a simplified, unitary probe structure in which the components of the probe are more readily machined, easily assembled and sealwelded. In addition, this invention provides a probe in which the sensing element is so constituted that, for either assembly or repair, a sensing element can easily be welded into place without causing any material change in the resistance characteristics of the sensing element. This result arises from an arrangement in which the weld on the sensing element is located on a relatively massive hub portion thereof, at a substantial distance from the relatively low resistance measuring portion of the probe, forming a positive, yet readily replaceable leak-proof seal suitable for use with high temperature and high pressure processes. The relatively massive hub portion of the sensing element substantially absorbs the added weld metal with negligible change in calibration and diffuses the welding heat so that the low resistance of the sensing element is not significantly affected. The massive hub portion also serves as a galvanic-action inhibitor in that it connects parts which often are of different metals and which, except for the presence of the massive hub portion, would undesirably give rise to galvanic-action between these metals, possibly affecting the resistance value of the sensing portion.

Another aspect of the invention provides an electrically resistive inner-end corrosion measuring portion having a wall of medium or heavy thickness which will not provide an erroneous high corrosion indication during the latter life of any probe which could be subject to pitting attack. Further, each test element is made strong and sturdy, so as not to fail by metal fatigue in fast moving streams even though the test element or sensing element may not be protected by an outer shield. In addition, each test element is designed so that the effects of rapidly varying process temperatures are almost completely nullified for general operation conditions, to the degree that normal fluctuating temperatures will not cause significant difficulties in accurately determining corrosion measurements. The probe construction also includes features which eliminate the common sources of electrical noise, crosstalk, hysteresis effect, and errors due to residual or thermocouple effects, particularly in instances where accuracy is required during corrosion monitoring in services involving elevated process temperatures. When used with compatible corrosion bridge measuring circuits, test sensors of the invention have a long life compared to the probes made by prior art techniques, without any loss of corrosion measuring sensitivity.

Still another aspect of the invention relates to a corrosion bridge measuring circuit which includes circuit means having parameters selected to be compatible with sensor design. The activity, or voltage output, of the bridge circuit is selected to accommodate a sensor which is sized as a function of the desired tracking range of the sensor and its electrical resistivity. The tracking rate is determined from the anticipated corrosion rate of corrosive medium, while the electrical resistivity is governed by the material from which the sensor is made. By sizing a probe to produce resistance values over an anticipated range as a function of the electrical resistivity of a given material and the anticipated corrosion range, the sensor and circuit combination can be utilized for a substantially longer period of time than can be utilized for a substantially longer period of time than sensors of the prior art. By developing a plurality of predesignated bridges, a table can be constructed to determine for an anticipated corrosion rate and a given resistivity of material, the appropriate bridge for which the probe can be used.

The sensitivity of the circuit to incremental corrosion measurement is greatest at the maximum activity or voltage output of the bridge, although the wall thickness of the sensor at depletion is generally thinner than may be desirable for certain circumstances. On the other hand, the sensitivity of the circuit is less at a lesser activity and the wall thickness of the sensor is greater.

The bridge circuit of the invention provides for a half bridge, which is half active and which possesses a relatively low corrosion bridge gage factor to produce a given output for a fully active bridge. The "gage factor" for these purposes may be considered to be the ratio of the resistance of the half active leg for a new sensor to the resistance of the half active leg at depletion. For a fully active bridge, the gage factor is at its maximum, and for less than a maximum bridge output voltage, the bridge gage factor has a lesser value. Therefore, the maximum gage factor for a bridge can be used to determine the physical dimensions of a sensing element which will produce a fully active bridge at maximum sensitivity. By maintaining bridge gage factors extremely low, the physical result is that the sensors will have a relatively large cross-sectional area for the corrosion measuring portion which will permit the sensor to be fabricated by machine operations.

In the invention, only a portion of the active arm of the bridge is exposed to the corrosive medium and the remaining portion of that leg must be covered for attachment of leads and contacts. By using bridges having low gage factors, a greater portion of the active leg may be covered and only a minor portion need be exposed to activity by corrosion to obtain the maximum bridge output. This feature also permits the construction of a sensor having a relatively large cross-sectional area and reduces the effect of temperature fluctuations on the output signal.

These and other objects and advantages of the system according to the invention will become apparent from the review of the detailed description of the invention which follows taken in conjunction with the accompanying drawing.

BRIEF SUMMARY OF THE INVENTION

Directed to achieving the foregoing aims and objectives, the apparatus according to the invention for measuring the corrosion of an electrically conductive material in a corrosive medium includes sensor means in combination with bridge circuit means. The sensor means comprises a closed end corrosion measuring portion preferably made from the same material as the conductive material on which the corrosive effect is to be measured.

The measuring portion has a relatively medium or heavy wall thickness and is adapted to be inserted into the corrosive medium. The measuring portion of the sensor is the first portion of a first electrical resistive element in a bridge circuit. Preferably, the measuring portion initially has a very low resistance. The extremely low sistance of the measuring portion is an advantage because the measuring portion is subjected to fluctuations in temperature of the corrosive medium so that the low resistance renders negligible the effect of such temperature fluctuations on the apparent resistance of the sensor when compared to the changes in resistance due to corrosion of the sensing element.

A hub portion adjoining, and preferably integral with, the measuring portion is in electrical circuit with the measuring portion. Teh hub portion is preferably formed from the same conductive material as the measuring portion. The hub portion is characterized as having a relatively thick wall compared to the measuring portion and therefore has a very low resistance. The hub portion constitutes the second portion of the first electrical resistive element in the bridge circuit. Like the measuring portion, the hub portion is also subjected to temperature variations in the corrosive medium, but in all likelihood to a slightly lesser degree.

The sensor includes a body portion adjoining the hub portion for housing the components of the sensor. A resistive element is disposed within the body portion of the sensor and is in electrical contact with the sensing element, for example, at the hub portion. A first portion of the resistive element adjacent the sensing element constitutes a third portion of the first electrical resistive element of the bridge circuit.

First circuit means and second circuit means, including electrical contacts and associated leads, are provided for defining a second portion of the resistive element as a second electrical resistive element having a predetermined reference resistance for use with the bridge circuit means. Additional circuit means are provided by way of contacts and associated leads for connecting certain of the electrical resistance elements to provide electrical connections to the bridge circuit means.

The bridge circuit means includes a source of electrical potential for simultaneously energizing the electrical resistance elements of the probe. The bridge includes means for measuring the output voltage from the bridge caused by an imbalance in the bridge circuit means to measure changes in the electrical resistance of the first portion of the first electrical resistance element to indicate the corrosion thereof.

It is a feature of the invention that the resistance value of the components of the bridge circuit are predetermined in such a manner to produce a predesignated plurality of bridge designations. It is an aspect of the invention to calculate the size of the sensing portion of the sensing means as a function of the resistivity of its material, the length of the sensing portion, and the anticipated corrosion rate to produce a resistance value which is compatible with at least one of the predesignated bridge circuits mentioned above. Thus, the output from the bridge circuit when connected to the probe can produce a useful output signal over a predetermined number of ranges. Preferably, each of the predesignated bridges has ten ranges.

It is another feature of the invention that the combined resistance values of the first and second portions of the first electrical resistance element is on the order of about 1 to about 10 percent of the combined electrical resistances of the first and second electrical resistant elements of the probe. This characteristic renders negligible the effect of changes in resistance caused by temperature fluctuations of the corrosive medium compared to the changes in resistance caused by the corrosive effects on the sensing element. Representative values of the resistances for the various resistive elements and the method of calculating the size of the measuring portion of the sensor are provided from which a table can be constructed readily relating a predesignated bridge to a given material at an anticipated corrosion rate. These and other features of the invention will become clear from the detailed description which follows.

BRIEF DESCRIPTION OF THE DRAWINGS

In the accompanying drawing:

FIG. 1 is a central longitudinal sectional view of a pre-designed corrosion sensor according to the invention and containing legends for correlating the resistive elements of the sensor to a bridge circuit;

FIG. 2 is a central longitudinal sectional view of a preferred form of probe according to the invention;

FIG. 3 is a circuit diagram of an equivalent electrical corrosion bridge measuring circuit related to the sensor for measuring the effect of corrosion of said sensor;

FIG. 4 is a circuit diagram of a circuit including a portion of the bridge circuit when connected to a probe for receiving data from the probe correlated with corrosion.

DETAILED DESCRIPTION OF THE PREFERRED EMBODIMENTS

Figure 5:
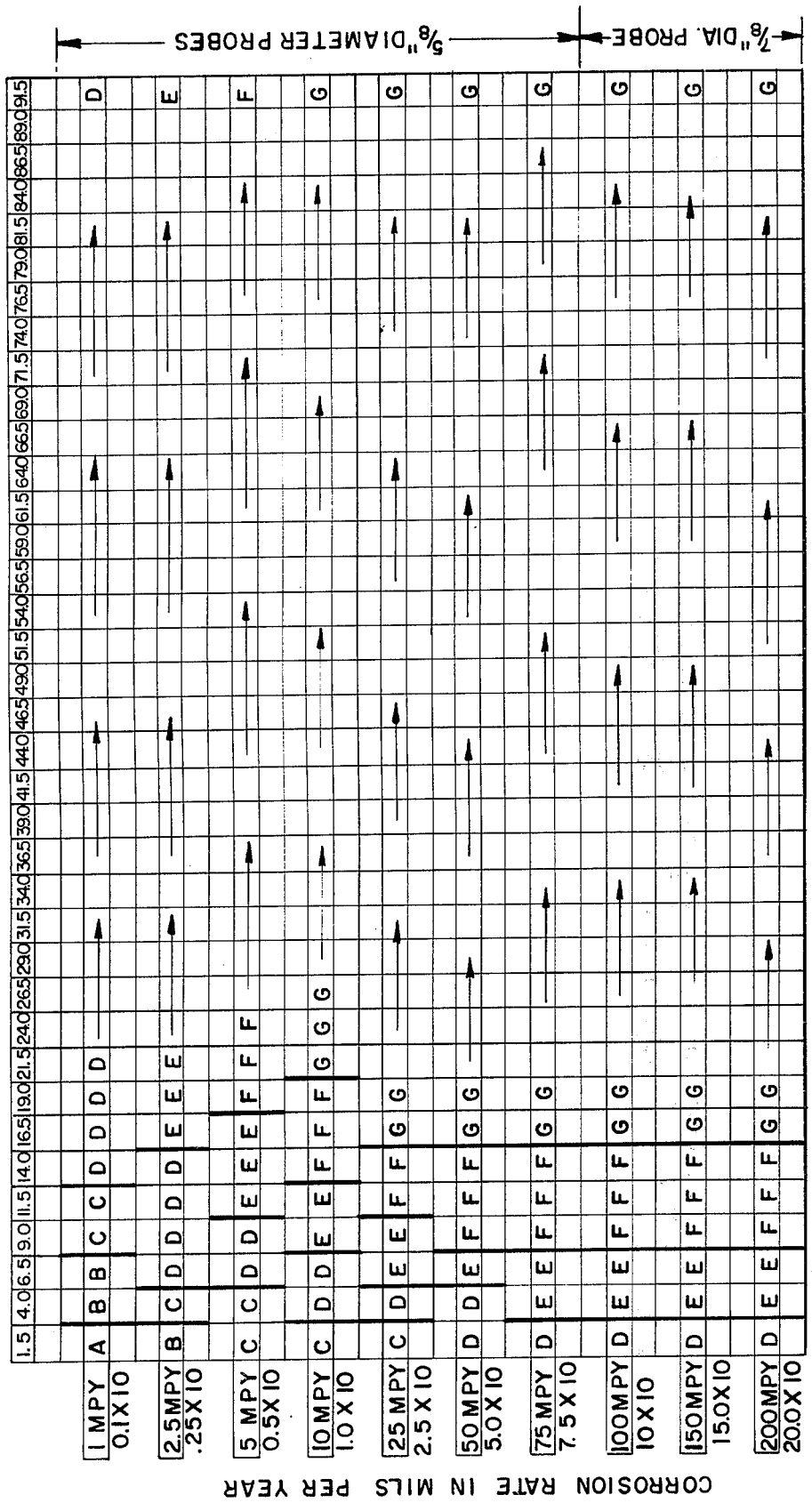
FIG. 5 is a table developed according to an aspect of the invention relating the bridge predesignations A through G to both the electrical resistivity of the sensing portion of the probe and the anticipated corrosion rate in mils per year.

FIGS. 1 and 2 together illustrate the essential components of a corrosion sensing probe, designated generally by the reference numeral 10. FIG. 1 illustrates the basic characteristics of the probe 10 and relates the resistive elements of the probe for use in connection with the explanation of the bridge circuit, while FIG. 2 illustrates the details of one preferred embodiment of the probe construction. Throughout the drawings, like elements are designated with the same reference numeral.

As shown in FIG. 1, the probe 10 includes a probe body 12, preferably manufactured from a straight metal pipe or other tubular metallic material. A metallic sensing element designated generally by the reference numeral 14, is disposed at the inner end of the probe body 12. By the construction of the probe of the invention, the principal electrically energized parts of the probe are located either partly or completely within the body of the probe. Throughout this specification, the reference to the "inner end" of the probe refers to the end of the probe 10 which is disposed in the fluid whose corrosion effect is being monitored. In the case of FIGS. 1 and 2, the "inner end" refers to the leftmost portion of the drawings. The term "fluid" for purposes of this description includes liquid, solid or gaseous phases, although monitoring of liquid corrosion is principally referred to.

The sensing element 14 is fixed into or onto the inner end of the probe body 12 and is immersed in the fluid to be monitored. Thus, the sensing element is subjected to fluctuations in temperature of the corrosive fluid. The chief function of the sensing element is to indicate the corrosiveness of the fluid when used in combination with related electrical instrumentation to be discussed later in this specification and to provide an indication of the condition of the materials within the container which are subjected to contact the corrosive fluid. Preferably, the sensing element is made from metal which is of like composition to the metal of the container wall, or of like composition to other dissimilar metals contained within the container, such as trays, tubes, bundles, and the like, or possesses a substantially equivalent capability for resisting corrosion of the container wall by reference to the readily determinable degree of corrosion of the sensing element. In the event that the metal of the wall of the container has a different capability for resisting corrosion compared to that of the sensing element 14, the relative capabilities of these two metals can be taken into account in determining the extent of corrosion of the wall of the container.

The sensing element 14 is defined in part by a measuring portion 16, also referred to in the drawings as the "first portion" which has a closed inner end 18. Preferably, the sensing element is tubular, although other geometrical configurations may be used, if desired. Preferably, the closure length is not electrically resistive.

The measuring portion 16 of the sensing element 14 is further characterized in that it includes a wall of medium or heavy thickness. The wall thickness is defined by the difference between the outside diameter 16a of the measuring portion 16 and the inside diameter 16b of the measuring portion 16 of the sensing element 14. The measuring portion 16 of the sensing element 14 thus includes a wall of medium or heavy thickness and is electrically resistive. The sensing portion has a very low resistance. Because the sensing portion comprises a part of the sensing element, it likewise is subject to fluctuation in temperature of the corrosive fluid.

The outer portion of the sensing element 14 adjoins the measuring portion 16, is homogeneously rigid therewith, and is in electrical contact with a relatively thick wall outer portion or hub section 20 which has a more substantial radial dimension than the measuring portion. The hub portion 20 extends, with a close fit, within the inner end of the body member 12 and is circumferentially welded thereto as shown by the weldment 22. The hub section 20 of the sensing element 14 is also referred to in the drawing as the "second portion" of the sensing element. The hub portion 20, like the sensing portion 14, has a very low resistance. Like the portion 14, the hub portion 20 is subjected to the fluctuations of temperature of the corrosive medium, although in all likelihood to a lesser degree.

A thin wall tube 21 is secured within the probe body 12 and is axially fitted over an outer portion of the hub section 20. The tube 21 may be filled with an insulating cement 23 to form a cartridge style probe.

A resistive element, designated generally by the reference numeral 24, and preferably made from a length of wire or other rigid structure, is contained within the interior of the probe body 12 and is secured, for example, by solder, within a recess 26 in the outer end of the hub section 20.

Electrical connections, designated by the reference numerals 18A and 18B, are provided on the interior wall 18C of the closed end 18 of the sensing element 14. Electrical connections are also provided, designated by reference numerals 24C, 24D, 24E, and 24F, on the resistive element 24. The locations are designated respectively by the numerals 30 and 32 along the resistive element 24 in FIG. 1.

As shown in phantom outline in FIG. 2, a perforated, protective shield 34, is held in place over and spaced from the sensing element 14 by being threaded, as at 36, onto the inner end of the body member 12.

All surfaces of the sensing element 14 which are exposed to corrosive fluid in the container are gradually corroded and/or eroded so that the walls of the element become somewhat thinner. Because of the relationship of the thickness of an electrical conductor to its electrical resistance, any corrosion which causes even a slight thinning of the wall of the medium or heavy wall thicknesss measuring portion 16 of the sensing element 14, will provide a perceptible increase in the resistance characteristic of that measuring portion 16. However, comparably slight corrosion and/or erosion of the relatively massive hub portion 20 of the sensing element 14 does not cause any significant material change in the resistance of that more massive portion. This invention, broadly like prior probes as shown, for example, in the U.S. Pat. No. 3,320,570, mentioned above, utilizes a perceptible change in the electrical resistance of the sensing element as a means for determining the corrosiveness of the fluid whose corrosiveness is being tested.

The measuring portion of the probe is normally in a resistance-balanced electrical circuit with other resistance elements, the resistance values of which are non-varying, since they are not in contact with the fluid being tested. Any determined imbalance of the circuit over a given time period thus indicates a resistance change only in the sensing element. Hence, such a resistance change is a useful indicator in determining the degree of corrosiveness of the fluid being tested. This invention includes, among other things, the improvement of having all the components of the normally resistance-balanced circuit embodies in or as a part of an improved unitary testing device.

As explained in the graphics accompanying FIG. 1, the sensing element 14 of the probe 10 electrically defines a first electrical resistance element while the resistive wire 24 defines a second electrical resistance element or reference resistive element for use in connection with the circuitry to be explained hereafter. The measuring circuit is basically a bridge circuit designed as an effective half bridge halfactive circuit.

As can be seen in FIG. 1, the first electrical resistance element is defined by three portions. The first portion is measuring portion 16 of the sensing element 14 and is denominated an "exposed-exposed" portion. This means that the measuring portion is exposed to the effects of corrosion and to the effects of temperature. The second portion of the first electrical resistance element is defined by the hub section 20 and is denominated as a "partially covered-partially exposed" portion, meaning that some of the hub section may be subject to the corrosiveness of the fluid and that the hub portion is subject to temperature variations of the fluid medium. A third portion of the first electrical resistance element is "covered" (or not affected by the corrosiveness of the fluid and insulated from temperature fluctuations) and is defined by the portion of the resistive element 24 between the connection 30 (the location of electrical points 24C and 24E) and the hub section 20.

The second electrical resistance element or reference element is defined by the portion of the resistive element 24 which exists between the contacts 30 and 32, or between the electrical points 24C and 24E, on one hand, and electrical points 24D and 24F, on the other.

As can be seen, it is an aim of the invention to design the sensing element 14 so that a very low proportion of the resistance of the element 14, on the order of 1 to 10 percent, is comprised of the sensing material. The remaining portions of the total resistance, on the order of 90 to 99 percent, is defined by the third portion of the first electrical resistance element and the second electrical resistance element. The advantages of these proportions will be discussed in greater detail. Effectively, the electrical resistance of the sensing portion 16 and the hub section 20, each of which is made of materials to monitor corrosion is precalculated to be only about 1 to 10 percent of the total resistance of the three portions of the first electrical resistance element.

As previously mentioned, the sensing element 14 is rigidly connected, in a fluid tight manner, substantially distal from the inner end portion 18 to the metal tubular probe body 12 to provide between the tubular body 12 and the inner end portion a highly conductive thick wall portion of the sensing element for the purpose of allowing a positive, leak-proof seal by the weldment 22 at that juncture. This construction does not interfere with the regulated resistivity values established during sensor calibration and also avoids material galvanic action between the metals of the inner end portion and the probe body. The probe body is preferably substantially self-contained or unitary and has an improved arrangement of supplemental resistant wires, discussed in connection with FIG. 2, within the probe body so that the probe includes all of the principal components of a double Kelvin bridge circuit which is relatively free of unwanted noise and signal errors.

As mentioned, the interior of the probe body 12 may be filled with insulating cement 23 to make a cartridge-style calibrated assembly. Such insulating cements are commercially available and are capable of resisting the high temperature of the probes which may be used. In any event, whatever encapsulation is used, it is not in contact with the process fluids being measured.

Turning now to the preferred embodiment of the invention shown in FIG. 2, the components of FIG. 2 which are common with those described in connection with FIG. 1 will not be described again in detail. The probe body 12 includes exterior threads 36 at the inner end thereof to receive mating threads on the perforated protector sensor shield 34. The probe body also includes threads 38 at the outermost end thereof for receiving a multiple-pin connecting plug 40 for providing a plug-in connection to an external power supply and signal takeoff instrumentation for connection to an appropriate instrumentation 46, which includes a portion of the bridge.

As is well known in the art, the probe 10 is adapted to project through a tubular sleeve member 48 through a wall 50 of a pipe or other container of fluid, the inside of the pipe or container being at the lefthand portion of the portion of the wall 50 illustrated in FIG. 2. The mounting of the probe may be similar to the mounting shown in FIG. 1 of U.S. Pat. No. 3,320,570, to which reference may be made for complete detail. Other methods of mounting the probe in a corrosion monitoring system are, of course, within the scope of this invention.

The several resistance elements described in connection with FIG. 1, or the resistance portions of the conductors, are connected to the pins of the plug 40 by suitable high temperature insulating wiring designated generally by the reference numeral 52 within the probe body 12. By way of a specific example, the insulation for each conductor may be woven glass sleeving.

Preferably, the resistance element 24 is a straight relatively stiff wire member. As previously explained, the outer end of the wire is connected from a solder connection point 24F thereof by an unsulated conductor 52a, for example, a copper wire, to a power pin 40F in the plug 40.

A first power pon 40A and a second power pin 40F in the plug 40, are connected to an alternating current power source (as also shown with corresponding reference numerals in FIGS. 3 and 4) by an insulating copper wire 52b which extends within the body member 12 and the interior bore 17 of the sensing element 14 to a contact 18A. The lead 18A is electrically connected to the wall 18C and is made of the same material as the sensor 14 to avoid thermocouple effects therebetween in high temperature service. The power supply is further connected from points 18A and 18B through the first and second electrical resistance elements in situ to a soldered connection 24F. The electrical point 24F is connected to a second insulated copper wire 52A which is connected to the second power pin 40F. The power circuit preferably supplies an electrical current of about 0.500 amperes at 0.5055 volts (see FIG. 3).

The resistive element 24 has tap-off connection points 24C and 24D which subdivide the wire into resistance portions 54 and 56. The resistance portion 54 of the element 24 corresponds to the third portion of the first electrical resistance element while the portion 56 corresponds to the second electrical resistance element.

A first bridge circuit comprising the first electrical resistance element leg extends from pin 40B in plug 40 by an insulated stainless steel wire 52d which extends through the interior bore 17 of the body member 12 and the insulated wire 52d through to the electrical contact 18B on the wall 18C. The lead 18B is preferably made of the same material as the sensor 14, again to avoid thermocouple effects. The circuit is completed through the measuring portion 14, the hub section 20 and the resistive segment 54 of element 24 (which together comprise the first electrical resistance element of the bridge), to the soldered connection point 24C thereof, and then through an insulated wire 52f which is connected to point 24C. The wire 52f is made of the same material as the element 54. The wire 52f is connected through an insulated wire 52g, preferably made from stainless steel, to a soldered connection pin 40C in the plug 40.

Synonymous with soldered connection point 24C, and at the same location on element 24 thereof, is a second soldered connection point 24E, from which an automatic gain control tap-point in the corrosion analyzer is supplied through a special circuit as described more fully in U.S. Pat. No. 3,821,642, to Seymour, incorporated by reference, extending from the point 30 through an insulating wire 52j made from the same material as element 24, thence through insulating lead 52k made from stainless steel, and to a soldered connection pin 40E in the plug 40.

The leads 52d, 52g, and 52i are generally made in a triplicate set of three leads braided together for the full length within the probe structure, to form a single trunk. Similarly, the leads 52 and 52b are braided with the three-wire trunk described above, also enveloping, without braiding, lead 52k, all forming a single first trunk, for the full length within the probe structure, consisting of a total of six lead wires, all pertaining to bridge resistance lead wires. The purpose of this construction is to subdue cross-talk and reduce electrical noise in the corrosion analyzer voltage output signal.

In certain circumstances, it has been found advantageous to electrically shield the resistive element 24 by wrapping it with an insulating material, such as an insulating tape, surrounded by a wrapping of an electrical conductor, such as aluminum foil. This construction further appears to reduce cross-talk and electrical noise within the probe structure and improves the stability of the output signals from the instrument.

The degree of corrosion measurement is obtained as a voltage output $E_o$ between points 40C and the center tap on the range selector switch 58 (see FIG. 3) due to the degree of imbalance of the corrosion bridge measuring circuit in use, as diagrammatically indicated in FIG. 3, thereby providing for ascertainment of the relative potentials of the two circuits of the bridge. A change in such relative potentials over a given time period permits a determination of the extent of corrosion of the sensing portion 16 of the sensing element 14 during that time period, and hence, a determination of the degree of corrosivity of the fluid within the container.

FIG. 3 depicts a circuit diagram of a Wheatstone bridge equivalent circuit which diagrammatically relates the resistances of the sensor to electrical components for determining an output voltage which is a function of the corrosion of the sensor. A source of power 71 preferably provides 0.005 volts to terminals 40A and 40F as discussed above, assuming lead resistances Ri and about $1\Omega$.

A resistor 60, preferably $100\Omega$, is connected to terminal 40B and to a terminal of the selector switch 58. A resistor 61, preferably $80\Omega$, is connected to the terminal 40D and to the other terminal of the selector switch 58. A resistor 62, preferably $20.2\Omega$, is connected between the two terminals of the range selector switch 58. A resistor (not shown), and having a value of about $183.5\Omega$, is connected between each tap of the switch 58 and is sized to provide an equivalent $20\Omega$ resistance network in parallel with resistor 62, which equivalent is in series with resistor 61.

The resistor 63, the resistor 64, and the resistor 65 are the circuit equivalents of the resistance of the respective portions of the first electrical resistance element of FIG. 1. The resistor 66 is the circuit equivalent of the second resistance element of FIG. 1. The output from the bridge is taken between the point 40C and the common connector 58a of the selector switch 58.

At the start of the corrosion monitoring, the bridge is symmetrical about the connection 60a between resistors 60 and 62 since the bridge is designed so that the parallel combination of the resistor 62 and the resistor network in the switch 58 provides an equivalent series resistance of $20\Omega$ in series with the resistance 61, those totaling $100\Omega$, the same resistance as resistance 60. This provides a symmetrical bridge at that point at the start of monitoring.

The bridge components are selected to provide a 10 volt output for a fully active bridge. At the start, with a new sensor with the selector switch in the 0 position, the bridge is balanced and the bridge output is 0 volts. As the sensor corrodes, the active resistance 63 increases, causing an increase in the bridge output voltage, which is sensed, up to the maximum of 10 volts. When the bridge output reaches 10 volts, the selector switch 58 is manually changed to the 1 position and the bridge is again symmetrical about the point 60a whereupon the bridge output reverts to 0 volts. This procedure is repeated throughout the 10 ranges of the selector switch. Thus, it can be seen that the selection of resistances of the bridge, including the physical dimensions of the sensor, produce a sensor which can be measured over a sequence of 10 ranges.

FIG. 4 illustrates a block diagram of the essential components of a signal conditioner and remote data acquisition system, designated generally by the reference numeral 70. The terminals, designated 40' and respectively labeled A-F, correspond to the terminals shown in FIG. 2 designated by the numerals 40A-40F.

An oscillator 71 is connected by leads 72 and 73 to the terminals A and F, respectively, of terminal block 40'. The resistors 60, 61, and 62 are connected in series circuit between the terminals 40'B and 40'D. The lead 66 is connected to a source of reference potential, such as ground, and to the common 58a of the selector switch 58 as described in connection with FIG. 3. The lead 74 is connected to the source of reference potential at lead 66 and to the terminal 40'E to provide a ground lead for the probe. The output from the probe on lead 65 is derived from terminal 40'C and is coupled by a transformer 76 to an amplifier 77.

The output from the oscillator 71 is also connected by leads 78 and 79 to a comparator circuit 80 having its output connected by a lead 81 to a synchronous detector 82. The signal from the comparator 80 is applied to the detector 82 to provide a reference signal for the synchronous detector. The detector circuit 82 provides a DC output signal which is provided to the filter 83, the output of which is between 0 and 10 volts DC per range for a fully active bridge. The details of such circuit 70 may be found in U.S. Pat. No. 3,821,642, which is herein incorporated by reference.

A voltage divider network designated generally by the reference numeral 85, is connected to the output of the filter comprising a resistor 86 in series with a resistor 87 wherein the output from that bridge is taken across the resistor 87. Thus, the combination of resistors 86 and 87 acts as a voltage divider to provide the desired 0 to 100 millivolt DC output to the circuit 89.

The circuit 89 transfers the voltage output signal to a current output signal, for example, in the 4 to 20 milliamp range and is a commercially available unit manufactured by Westinghouse Corporation or its equivalent. For purposes of this disclosure, the circuit 89 is a voltage to current transmitter, as is well known in the art.

The phantom outline, designated by the reference numeral 90, indicates the control room which is remote from the probe. A positive bias source, designated generally by the reference numeral 91, is provided to provide actuation for the transmitter 89 through the resistor 92 while the resistor 93 is connected in circuit with the metering on the transmission unit and is connected to an output load, designated generally by the reference numeral 94.

Once the design criteria for the bridge circuit has been established as discussed above, the sizing of the physical dimensions of the sensing element may be determined. The bridge criteria includes a number of factors. It is, for example, desirable for the flow of current from the AC power source to be on the order of 0.500 amperes, or less, to prevent undue heating of the sensor. As previously indicated, it had been desirable to provide a 10.0 volt output for a fully active bridge for each range, and this value was selected because of its acceptability in the art as a typical range of output voltages from sensing probes and for its compatibility with standard equipment. Thus, given the desired current limitation and the desired bridge output, the relative ranges of resistance values for both the active and the reference element leg of the bridge becomes somewhat established in the range of about 0.0055 ohms for each leg. Once these relative values are established, the physical dimensions of the sensor may be determined within reasonable approximation.

Such a value is also advantageous in that probes can be produced which are compatible with existing installations in terms of the diameter of the sensing element, length of insertion in process media, and the like. By way of example, it is generally a limitation on the insertion length of the probe to be on the order of 6 to 8 inches.

As previously indicated, it is a further design criteria that the bridge be symmetrical in order to nullify thermocouple effects at high temperatures when using electrical leads and attachment weldments made from metals dissimilar to the sensor material.

It has been determined in the course of the development of the invention that it is desirable to maintain the bridge gage factor of a fully active bridge at a value of 1.500 or less. Such a value of the gage factor permits the production of a sensing element having dimensions approximately in the range of acceptability as discussed above.

Thus, in determining the sizing of the sensor, it is first necessary to establish a satisfactory internal diameter to accommodate the leads within the bore of the probe and a typical value chosen as on the order of 0.136 inches. The next factor of interest in sizing the sensor is the anticipated corrosion rate of the sensor in its corrosive environment. Since it has been established that it would be desirable to utilize the sensor over 10 ranges, an anticipated corrosion rate of 50 mils per year, for example, would mean roughly that the sensor must be responsive in conjunction with the bridge to monitor a 5 mil penetration depth of corrosion per range. FIG. 5 sets forth the range of values from 1 mil per year to 200 mils per year and relates each of these anticipated corrosion rates to the 10 range feature.

Thus, by knowing the anticipated corrosion rate per range of the material and the established I.D., the sum of the I.D. of the sensor, plus the anticipated depth of penetration over the 10 ranges, plus the thickness of the wall of the sensor at depletion should equal the wall thickness of the sensor at the beginning of its measuring range.

However, such an anticipated O.D. for the sensor must, in combination with a selected length of the sensing element, produce a resistance value which is compatible with the bridge which is discussed above. It has been advantageous to determine the range of resistance values for materials of given resistivity on a computer by calculating the electrical resistance of the sensing element according to the general equation (1):

$$R = \rho \times \frac{l}{A} \qquad (1)$$

R = p × 1/A (1)
which, for a cylindrical construction of the embodiment shown, is transformed into the equation (2);

$$R = \frac{4\rho}{\pi} \left[ \frac{l}{D_o^2 - D_i^2} \right] \qquad (2)$$

where,
R is the resistance of the sensing element in ohms,
$l$ is the length of the sensing element,
$\rho$ is the resistivity of the material in $\mu\Omega$-cm,
$D_o$ is the outside diameter of the sensing element, and $D_1$ is the inside diameter of the sensing element.

Thus, for a preselected material of a given resistivity, generally specified by the consumer, a series of calculations can be made to calculate precisely the physical dimensions of the sensing element. A typical way of making this determination is to first approximate an outside diameter as indicated above for a given material and to assume the I.D. Thereafter, the area of the I.D. can be calculated, as well as the area of the proposed O.D., for the total depth of penetration over the 10 ranges.

The gage factor for the fully active bridge providing a 10.0 V output is 1.444444. Thus, at depletion, the resistance of the exposed leg must be increased by reason of the reduction of the cross-sectional area due to corrosive attack by the gage factor. But, only a portion of the first electrical element leg changes resistance; therefore, it is convenient in making size calculations to introduce a z factor which is useful in determining what portion of the total leg resistance shall be designed as active, leaving the remaining portion inactive. Accordingly, equation (3) is as follows:

$$x + Y = 1.444444$$
$$z + Y = 1.000000 \quad (3)$$

where, $x$ = the proportion of the active leg resistance of the sensor at depletion;

$Y$ = the proportion of the leg resistance of the sensor attributable to the inactive portion; and $z$ = the proportion of the active leg resistance of the sensor at start.

Further, the cross-sectional areas of the sensor "new" and the sensor "depleted" can be calculated for any assumed O.D. and I.D. The ratio of the new cross-sectional area to the cross-sectional area of the sensor at depletion must be equivalent to the ratio of $x/Y$ as set forth above. Therefore, the value of $x$ in terms of $z$ can be found. By substitution in equation (3) above, the value of $z$ can be calculated.

After determining the resistance of the sensor per unit for an assumed I.D. and O.D. at a given resistivity, the resistance per unit length can be determined. Thereafter, the ratio of the unit resistance may be related to the required leg resistance of the active leg of the bridge. This ratio, when multiplied by the z factor, will produce the length of the measuring portion of the sensor in terms of inches.

Typically, such calculations are performed on a computer since fitting a predetermined length, e.g. 1.750 inches to a predetermined bridge is a matter of repetitive calculations based on changing assumptions. For completeness, a portion of a printout performing such calculations for a resistivity of 4.00 $\mu\Omega$-cm is reproduced and attached as Appendix A to this application.

Thus far, a fully active bridge, producing a 10 volt maximum output under the amplification conditions described in connection with FIG. 5 has been described. Because there are combinations of circumstances involving the anticipated corrosion rate in mils per year and electrical resistivity which will not be able to provide a 10 volt output for a fully active bridge on a 10 range basis, the concept of predesignated bridges has been developed. For purposes of simplicity, a table relating bridges designated A through G is attached hereto as Appendix B.

FIG. 5 illustrates the preferred relationship of the predesignated bridges having multi-range capabilities for materials of various resistivities for use with anticipated corrosion rates ranging from 1 mil per year to 200 mils per year. The value of such a chart indicates readily to the consumer the type of corrosion sensor which can be made available and its output on a 10 range basis. For situations involving less than a 10 volt maximum output per range, such as that produced by bridges A through G, accommodations will need to be made in the circuitry to receive such signals, either by reducing the number of receiving ranges in connection with given equipment or by sacrificing sensitivity on a per range basis.

The gage factors for the various bridges have been calculated as described above and it can be seen that an A bridge is much more responsive than a G bridge on a per range basis as described above.

Figure 6:
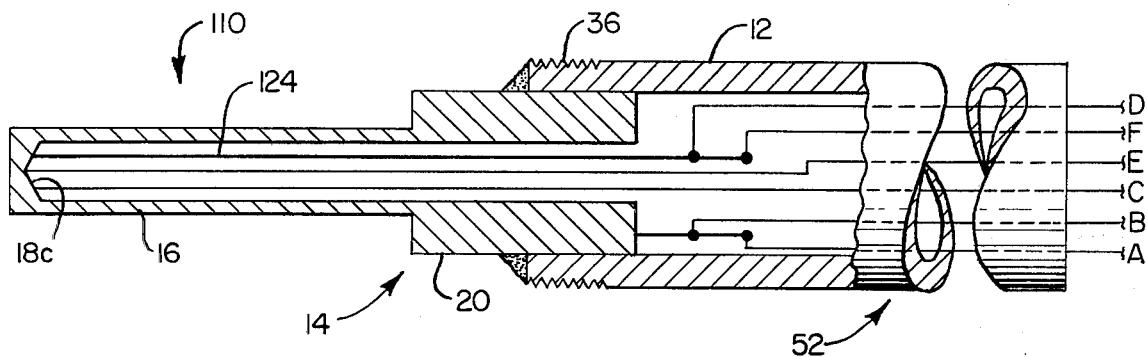
FIG. 6 is an alternate embodiment of a probe which may be used with the bridges according to the invention.

FIG. 6 illustrates an alternative probe embodiment capable of use with the bridges according to the invention. The embodiment of FIG. 2 and like reference numerals have been utilized. The principal differences between the embodiment of FIG. 6 and that shown in FIG. 2 reside in the connection of the resistive element 24. Thus, the embodiment of FIG. 6 includes a resistive element 124 which is connected to the interior of the probe 18C rather than to the hub section.

The probe, designated by the reference numeral 110, can be utilized in conjunction with the circuitry of FIG. 4 and is otherwise similar in operation to the embodiments previously described.

Because the interior bore 17 of the embodiment of FIG. 6 must be sized to accommodate three leads rather than two, as a general proposition, the I.D. of the sensing element must be slightly larger to accommodate the leads, which can present difficulties in designing the sensor as described above. On the other hand, one of the advantages of the embodiment of FIG. 6 is that the reference element 124, being largely disposed within the interior bore of the sensing element 24, is more responsive to temperature variations in the process fluids.

The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

APPENDIX A

| O.D. (New) | Area (1) (Area Depleted) | Area (2) (Area Remaining) | Area (I.D.) | Ratio of $\frac{A_1 + A_2}{A_2}$ | Z | Length |
|---|---|---|---|---|---|---|
| 0.630500 | 0.312220 | 0.221035 | 0.014527 | 0.441555 | 0.083879 | 87.207898140 |
| 0.383250 | 0.115360 | 0.063013 | 0.014527 | 2.079622 | 0.034306 | 12.081016064 |

APPENDIX A-continued

| O.D. (New) | Area (1) (Area Depleted) | Area (2) (Area Remaining) | Area (I.D.) | Ratio of $\frac{A_1 + A_2}{A_2}$ | Z | Length |
|---|---|---|---|---|---|---|
| 0.277010 | 0.060267 | 0.024608 | 0.014527 | 4.536953 | 0.010471 | 1.672794640 |
| 0.277976 | 0.060688 | 0.024878 | 0.014527 | 4.459598 | 0.010706 | 1.725938141 |
| 0.278428 | 0.060886 | 0.025004 | 0.014527 | 4.424541 | 0.010815 | 1.751079172 |
| 0.278413 | 0.060879 | 0.025000 | 0.014527 | 4.425698 | 0.010812 | 1.750238776 |

| Bridge Designation | Gage | Output | Range |
|---|---|---|---|
| G | 1.444444 | 10.0 V DC | 10 |
| F | 1.200000 | 5.0 V DC | 10 |
| E | 1.075472 | 2.0 V DC | 10 |
| D | 1.037037 | 1.0 V DC | 10 |
| C | 1.018349 | 500 mV DC | 10 |
| B | 1.007299 | 200 mV DC | 10 |
| A | 1.003643 | 100 mV DC | 10 |

What is claimed is:

1. Apparatus for measuring corrosion of an electrically conductive material in a corrosive medium, said apparatus including probe means in combination with bridge circuit means, said probe means comprising:
   a closed end corrosion measuring portion made from such conductive material and adapted for insertion into said corrosive medium, said measuring portion being a first portion of a first electrical resistance element in said bridge circuit means, said measuring portion having a relatively low resistance, said measuring portion being subjected to fluctuation of temperatures in said corrosive medium;
   a hub portion adjoining said measuring portion and in electrical circuit therewith, said hub portion being formed from such conductive material and having a relatively thick wall compared to said measuring portion, and further having a very low resistance, said hub portion being a second portion of a first electrical resistance element in said bridge circuit means, said hub portion being subjected to temperature variations in said corrosive medium;
   a body portion adjoining said hub portion;
   a resistive element within said probe means and in electrical circuit therewith, said resistive element having a very low electrical resistance, a first portion of said resistive element being a third portion of a first electrical resistance element;
   first circuit means and second circuit means for defining a second portion of said resistive element as a second electrical resistance element in said bridge circuit means;
   additional circuit means connected to at least some of said first and second electrical resistance elements to provide electrical connections to said bridge circuit means;
   a source of electrical potential in said bridge circuit means for energizing said electrical resistance elements simultaneously, said bridge circuit including means for measuring the output voltage due to an imbalance in said bridge circuit means thereby to measure changes in the electrical resistance of the first portion of the first electrical resistance element to indicate the corrosion of said measuring portion.

2. The apparatus as set forth in claim 1 wherein said bridge circuit means includes multi-range resistance means for bridge imbalance over a plurality of resistance values of said multi-range resistance means.

3. The apparatus as set forth in claim 2 wherein the resistance values of said bridge circuit means are predetermined to produce a predesignated plurality of bridge designations.

4. The apparatus as set forth in claim 3 wherein the size of the measuring portion of the probe is determined as a function of the resistivity of its material, the length of the sensing portion, and the anticipated corrosive rate of the corrosive medium on the conductive material to produce a resistance value which is compatible with at least one of said predesignated bridge circuit means so that said bridge circuit means can be balanced over said predetermined multiranges.

5. The apparatus of claim 1 wherein said sensing portion is of a generally tubular construction and is integral with said hub portion.

6. The apparatus of claim 1 wherein the combined resistance value of said first and said second portions of said first electrical resistance element is on the order of about one to ten percent of the combined electrical resistance of said first and second electrical resistance elements to render negligible the effect of the resistance changes caused by the temperature fluctuations of said corrosive medium as opposed to the corrosive effects of said sensing elements.

7. The apparatus as set forth in claim 6 wherein the physical size of the sensing portion is partially controlled by the gage factor of the gridge circuit which is at maximum for a fully active bridge.

8. The apparatus of claim 1 wherein said resistive element is a wire.

9. The apparatus of claim 3 wherein said predesignated plurality of bridge designations are characterized about as follows:

| Designation | Ranges | Output | Gage Factor |
|---|---|---|---|
| A | 10 | 100 mV DC | 1.003643 |
| B | 10 | 200 mV DC | 1.007299 |
| C | 10 | 500 mv DC | 1.018349 |
| D | 10 | 1.0 V DC | 1.037037 |
| E | 10 | 2.0 V DC | 1.075472 |
| F | 10 | 5.0 V DC | 1.200000 |
| G | 10 | 10.0 V DC | 1.444444 |

10. The apparatus of claim 1 wherein the wall of the hub portion is sufficiently thick to permit a weld thereon which will not affect the precalibration of the resistance of the hub portion.

11. A sensor for a probe for measuring corrosion of an electrically conductive material in a corrosive medium, comprising:

a sensing portion which includes a measuring portion made from a conductive material and adapted for insertion into a corrosive medium, said measuring portion when new having a predetermined wall thickness and a very low resistance, said measuring portion being adapted to constitute a first active portion of a leg of the bridge circuit; and a hub portion made from a conductive material in electrical circuit with said measuring portion, said hub portion having a relatively large wall thickness and a very low resistance, said hub portion being adapted to constitute a second inactive portion of said leg of said bridge circuit;

resistive element means in electrical circuit with said sensing portion for providing from a portion thereof a reference resistance in another leg of said bridge circuit, another portion of said resistive element means being a third inactive portion of said leg of said bridge circuit;

circuit means for providing a source of power to and for sensing the resistance of said measuring portion, said hub portion and said resistive element means; and said sensor being further characterized in that said measuring portion and said hub portion constitute about 1 to about 10 per cent of the combined resistance of said leg and said another leg of said bridge circuit.

12. The sensor as set forth in claim 11, wherein said measuring portion has an integrally closed end, is made from the same material as said hub portion, and is integral therewith.

13. The sensor as set forth in claim 11, wherein said resistive element is a wire secured to an end of the hub portion opposite said measuring portion.

14. The apparatus as set forth in claim 1 wherein said resistive element is located within said body portion and in electrical circuit with said hub portion.

15. The apparatus as set forth in claim 1 wherein said resistive element is located within said closed end measuring portion and in electrical contact with said measuring portion.

* * * * *